United States Patent [19]

D'Arrigo

[11] Patent Number: 4,684,479

[45] Date of Patent: Aug. 4, 1987

[54] SURFACTANT MIXTURES, STABLE GAS-IN-LIQUID EMULSIONS, AND METHODS FOR THE PRODUCTION OF SUCH EMULSIONS FROM SAID MIXTURES

[76] Inventor: Joseph S. D'Arrigo, 23A Brickyard Rd., Farmington, Conn. 06032

[21] Appl. No.: 765,917

[22] Filed: Aug. 14, 1985

[51] Int. Cl.$^4$ .................. B03D 1/00; B01F 17/30; B01F 17/36
[52] U.S. Cl. .................. 252/307; 252/356; 252/61; 252/DIG. 1
[58] Field of Search ........... 252/307, 356, 61, DIG. 1; 514/945; 128/697

[56] References Cited

U.S. PATENT DOCUMENTS

| | | | |
|---|---|---|---|
| 3,936,391 | 2/1976 | Gabby et al. | 252/307 X |
| 4,085,059 | 4/1978 | Smith | 252/307 X |
| 4,235,734 | 11/1980 | Scherubel | 252/307 X |
| 4,466,442 | 8/1984 | Hilmann et al. | 128/653 |
| 4,495,224 | 1/1985 | Rigler | 427/222 |
| 4,515,775 | 5/1985 | Vanlerberghe | 424/70 |

OTHER PUBLICATIONS

Sebba; Microfoams, J. Colloid and Interface Science, vol. 35, No. 4, Apr. 1971, pp. 643–646.
Bernd, "Study of the Surface Films of Gas Nuclei . . . Part IV . . . ", Naval Ship Research & Dev. Center (1967).
Levine et al, "Microbubbles Have Intracardiac Velocities Similar to Those of . . . ", *J. Am Coll. Cardiology* 3, 28–33 (1984).
Corday et al, "Seminar on Contrast Two-Dimensional Echocardiography . . . ", *J. Am. Coll. Cardiology* 3, 1–5 (1984).
Feinstein et al, "Two-Dimensional Content Echocardiography. I. In Vitro . . . ", *J. Am. Coll. Cardiology* 3, 14–20 (1984).

*Primary Examiner*—John F. Terapane
*Assistant Examiner*—Catherine S. Kilby
*Attorney, Agent, or Firm*—Kramer, Brufsky & Cifelli

[57] ABSTRACT

Surfactant mixtures for the production of stable gas-in-liquid emulsions are provided comprising:
(a) a member selected from the group consisting of glycerol monoesters of saturated carboxylic acids containing from about 10 to about 18 carbon atoms and aliphatic alcohols containing from about 10 to about 18 carbon atoms;
(b) a sterol-aromatic acid ester;
(c) a member selected from the group consisting of sterols, terpenes, bile acids and alkali metal salts of bile acids;
(d) a member selected from the group consisting of sterol esters of aliphatic acids containing from 1 to about 18 carbon atoms; sterol esters of sugar acids; esters of sugar acids and aliphatic alcohols containing from about 10 to about 18 carbon atoms; esters of sugars and aliphatic acids containing from about 10 to about 18 carbon atoms; sugar acids; saponins; and sapogenins; and
(e) a member selected from the group consisting of glycerol, glycerol di- or triesters of aliphatic acids containing from about 10 to about 18 carbon atoms and aliphatic alcohols containing from about 10 to about 18 carbon atoms;
said components being present in said mixture in a weight ratio a:b:c:d:e of 2–4:0.5–1.5:0.5–1.5:0–1.5:0–1.5.

Processes are also provided for forming stable gas-in-liquid emulsions from said surfactant mixtures.

13 Claims, 1 Drawing Figure

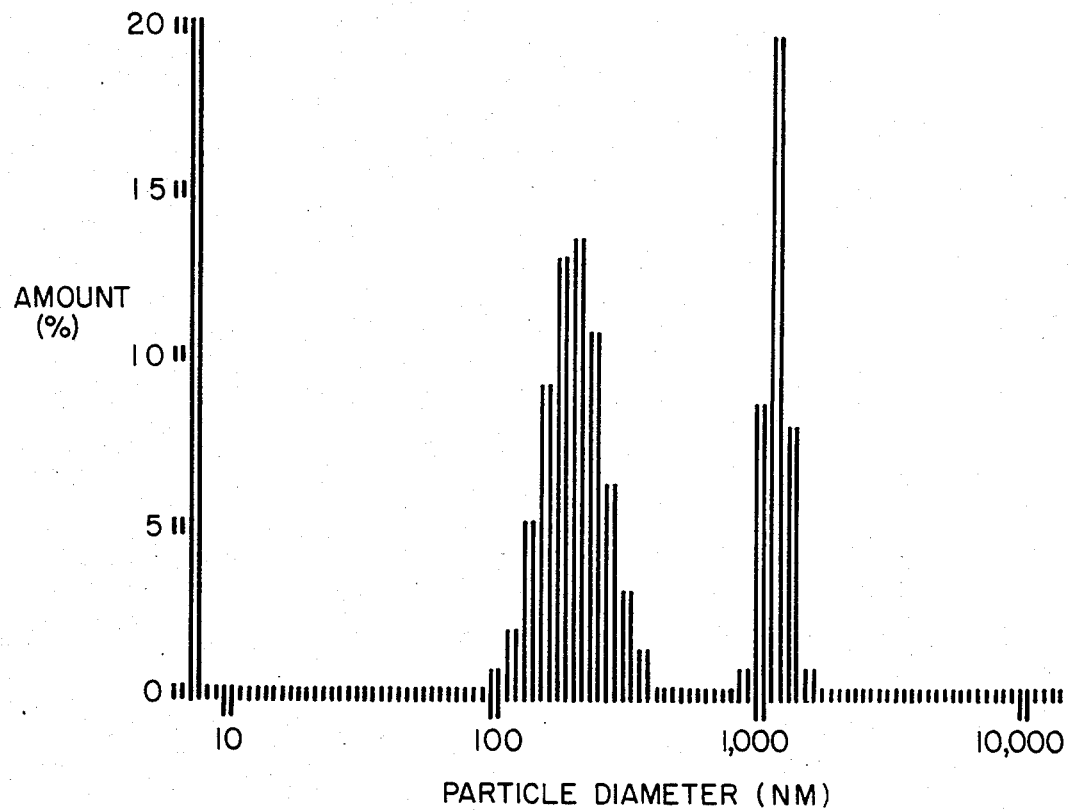

SURFACTANT MIXTURES, STABLE GAS-IN-LIQUID EMULSIONS, AND METHODS FOR THE PRODUCTION OF SUCH EMULSIONS FROM SAID MIXTURES

This invention relates to surfactant mixtures, stable gas-in-liquid emulsions, and methods for the production of such emulsions from said surfactant mixtures. More particularly, this invention relates to surfactant mixtures useful in the formation of suspensions of long-lived gas microbubbles in aqueous or oil-based media and to methods for the production of said gas microbubbles from said surfactant mixtures.

The occurrence of dilute gas-in-liquid emulsions in natural waters has become of great significance in many fields of fundamental and engineering sciences. Specifically, the existence of long-lived gas microbubbles in fresh water, sea water and other aqueous liquids including physiological fluids and the utility thereof in various applications has been studied by numerous investigators for more than 25 years. Despite this attention, no one prior to the instant invention has determined the physiochemical/biochemical mechanism by which such gas microbubbles (0.5–100 $\mu$m in diameter) are stabilized.

Due to the understanding of the physicochemical/biochemical mechanism achieved in accordance with the present invention, it is now possible to produce relatively concentrated, significantly stable (hours to several days), gas-in-liquid emulsions in both aqueous and oil-based media.

The ability to synthetically produce stable gas-in-liquid emulsions in aqueous and/or oil-based media is of significant importance in varied fields: acoustic and hydrodynamic cavitation, commercial oil recovery, hydraulic and ocean engineering, waste-water treatment, chemical oceanography, meteorology, marine biology, food technology, echocardiography, decompression sickness, and the like.

Many of these applications derive from the fact that persisting microbubbles affect the accoustical and the physicochemical characteristics of water, or other liquid media, increasing attenuation, scattering ultrasonic energy, changing speed of propagation, and grossly reducing the tensile strength. Artificial enhancement of tensile strength, in particular, obtained through low-cost chemical destruction of surfactant-stabilized microbubbles in water, is advantageous in order to improve the performance of devices normally limited in maximum output by cavitation, such as ship sonar, pumps, turbines, and propellers. The potential gains, such as the prevention of cavitation damage, obtaining a greater output from a given size or weight of equipment, i.e., an increase in return for a given economic investment, render knowledge of synthetic microbubble production quite useful. Separate, more fundamental considerations, include the fact the microbubble populations, well known by marine biologists to exist in the upper ocean, can become attached to particles within the water column; this attachment affects the settling rates of marine detritus and, hence, has an impact on the ocean food chain. Also, bursting of bubble populations at the sea surface, with the concomitant production of a sea-salt aerosol and the ejection of organic material into the atmosphere is of special interest to meteorolgists, oceanographers and environmental specialists.

Still further, although adsorptive bubble separation has been used commercially for more than half a century (principally in froth floatation to separate minerals from ores), the related process of microfloatation (requiring much smaller bubble sizes) was developed more recently for efficiently removing various colloidal pollutants from water and has proven to be a viable procedure for the treatment of water and waste waters. The process utilizes frothing agents to promote the formation of microbubbles and these amphilic substances contribute to the maintenance of a stable foam.

Another area in which stable microbubble production can be used to advantage is the area of two-phase bubbly flows. In these systems, two-phase flows occur, e.g., a motive liquid and an entrained gas. Typical of this type of system is the entrainment and pumping of corrosive fumes that are otherwise difficult to deal with.

In the medical field, the ability to produce stable microbubbles of uniform dimensions is of special importance as a source of contrast agents for echocardiography, wherein injected air microbubbles have been shown to travel with intracardiac velocities similar to those of red blood cells.

Another clinical application for the non-toxic, synthetic microbubbles of the present invention is in the ultrasonic monitoring of local blood flow in the abdomen. Such refined ultrasonic blood flow measurements, utilizing locally injected synthetic mirobubbles, provide better clinical detection of tumor neovascularization as well as any subtle changes in the normal vascularization patterns of organs neighboring abdominal masses. Hence, through the use of synthetic microbubbles, ultrasound can now provide much earlier diagnosis of abdominal masses; this early detection can well improve treatment of several classes of serious abdominal cancers, most notorious of which is pancreatic cancer.

Accordingly, it is an object of the present invention to provide a surfactant mixture for the production of stable gas-in-liquid emulsions.

It is another object of the present invention to provide relatively concentrated, significantly stable gas-in-liquid emulsions in aqueous and/or oil-based media.

It is still a further object of the present invention to provide processes for the preparation of stable gas-in-liquid emulsions from dry, powdery surfactant mixtures exhibiting long shelf life.

These as well as other objects and advantages are accomplished by the present invention which, in one embodiment, provides a surfactant mixture for the production of stable gas-in-liquid emulsions comprising:

(a) a member selected from the group consisting of glycerol monoesters of saturated carboxylic acids containing from about 10 to about 18 carbon atoms and aliphatic alcohols containing from about 10 to about 18 carbon atoms;

(b) a sterol-aromatic acid ester;

(c) a member selected from the group consisting of sterols, terpenes, bile acids and alkali metal salts of bile acids;

(d) a member selected from the group consisting of sterol esters of aliphatic acids containing from one to about 18 carbon atoms; sterol esters of sugar acids; esters of sugar acids and aliphatic alcohols containing from about 10 to about 18 carbon atoms, esters of sugars and aliphatic acids containing from about 10 to about 18 carbon atoms; sugar acids; saponins; and sapogenins; and (e) a member selected from the group consisting of glycerol, glycerol di or triesters of aliphatic acids containing from about 10 to about 18 carbon atoms and aliphatic alcohols containing from about 10 to about 18 carbon atoms;

said components being present in said mixture in a weight ratio a:b:c:d:e of 2-4:0.5-1.5:0.5-1.5:0-1.5:0-1.5.

The present invention will be more readily understood upon consideration of the drawing where, in the sole figure, is graphically illustrated the particle size distribution of stable gas microbubbles obtained in accordance with the present invention as determined by dynamic-light-scattering measurements.

The surfactant mixtures of the present invention are best obtained in dry powdered form. The stable gas-in-liquid emulsions of the present invention are obtained by forming at least a substantially saturated solution of the surfactant mixture in an aqueous or oil-based media, i.e., which is generally obtained by admixing from about 0.02 to about 0.4 gm of the surfactant mixture with 100 cc of the liquid medium (which ranges from slightly less than saturated to in excess of saturation depending upon the precise surfactant mixture used and the liquid medium employed), and vigorously shaking the resultant mixture for from about 2 to about 10 seconds in the presence of air under ambient conditions of temperature and pressure. High concentrations of stable gas microbubbles i.e., concentrated gas-in-liquid emulsions, are thereby readily obtained. These emulsions remain stable for from about two hours to about two-three days under normal ambient conditions.

The surfactant mixture of the present invention is, in its simplist form, a three component admixture of components a, b and c as defined hereinabove. The use of components d and e, defined hereinabove, while optional, has been found to be advantageous (although not necessary) in obtaining long term stability and uniform microbubble size.

Component a of the surfactant admixture is a member selected from the group consisting of glycerol monoesters of saturated carboxylic acids containing from about 10 to about 18 carbon atoms such as, for example, glycerol monolaurate, glycerol monopalmitate, glycerol monostearate, glycerol monomyristate, and the like. In addition, component a can be an aliphatic alcohol containing from about 10 to about 18 carbon atoms such as, for example, n-decyl alcohol, lauryl alcohol, myristyl alcohol, cetyl alcohol, n-octadecyl alcohol and the like.

Component b of the surfactant mixture can be a sterolaromatic acid ester, i.e. an ester formed from a sterol such as ergostenol,, colocynthsterol, 7-dehydrocholesterol, lanosterol, ergosterol, cholesterol, sitosterol, phytosterol and the like and an aromatic acid such as benzoic acid, naphthoic acid, anthroic acid and substituted derivatives thereof such as phenyl acetic acid, o-toluic acid, m-toluic acid, p-toluic acid, phthalic acid, isophthalic acid, terephthalic acid, salicylic acid, p-hydroxybenzoic acid, and the like. Typical of such sterolaromatic acid esters are cholesterol benzoate, lanosterol benzoate, cholestanol benzoate, ergosterol phenylacetate, sitosterol phthalate, phytosterol salicylate, and the like.

Component c of the surfactant mixture is a member selected from the group consisting of sterols, terpenes, bile acids, and alkali metal salts of bile acids. Any of the sterols described hereinabove can be suitably employed as component c of the surfactant mixture. Similarly, terpenes such as terpineol, vitamin A, citronellol, and the like can also be employed. Also, bile acids and the alkali metal salts thereof also can be suitably employed. Typical bile acids such as cholanic acid, choleic acid, , deoxycholic acid, cholic acid, chenodeoxycholic acid and the like can be suitably employed. Typical alkali metal salts of the bile acids are sodium cholate, potassium cholanate, lithium cholate, potassium cholate, sodium chenodeoxycholate, and the like.

Optional component d is a member selected from the group consisting of sterol esters of aliphatic acids containing from 1 to about 18 carbon atoms. Typical of such sterol aliphatic acid esters are cholesterol acetate, cholesterol n-butyrate, cholesterol iso-butyrate, cholesterol palmitate, cholesterol stearate, lanosterol acetate, ergosterol palmitate, phytosterol n-butyrate, and the like. Typical of the sterol esters of sugar acids useful in the present invention are cholesterol glucuronide, lanosterol glucuronide, 7-dehydrocholesterol glucuronide, ergosterol glucuronide, cholesterol gluconate, lanosterol gluconate, ergosterol gluconate, and the like. Typical esters of sugar acids and aliphatic alcohols containing from about 10 to about 18 carbon atoms include esters such as lauryl glucuronide, stearoyl glucuronide myristoyl glycuronide, lauryl gluconate, stearoyl gluconate, myristoyl gluconate, and the like. Esters of sugars and aliphatic acids containing from about 10 to about 18 carbon atoms include sucrose laurate, fructose laurate, sucrose palmitate, sucrose stearate, and the like. In addition, sugar acids, per se, can be employed such as glucuronic acid, gluconic acid, saccharic acid, polyuronic acids and the like. Similarly, saponins such as sarsasapogenin, smilagenin, and the like can also be employed. Also, sapogenins can be suitably employed. Typical sapogenins are hederagenin, oleanolic acid, digitoxigenin, and the like.

Component e is member selected from a group consisting of glycerol, glycerol di- or triesters of aliphatic acids containing from about 10 to 18 carbon atoms and aliphatic alcohols containing from about 10 to about 18 carbon atoms. Illustrative of suitable glycerol di- or triesters of aliphatic acids containing from about 10 to about 18 carbon atoms are glycerol dilaurate, glycerol trilaurate, glycerol dipalmitate, glycerol tripalmitate, glyerol distearate, glycerol tristearate, glycerol dimyristate, glycerol trimyristate, and the like. The aliphatic alcohols containing from about 10 to about 18 carbon atoms which are suitable for use in conjunction with the present invention include n-decyl alcohol, lauryl alcohol, myristyl alcohol, cetyl alcohol, n-octadecyl alcohol and the like.

The surfactant mixture of the present invention can be readily prepared by admixing components a through e in a weight ratio a:b:c:d:e: of 2-4:0.5-1.5:0.5-1.5:0-1.5:0-1.5, respectively. Preferably, the components of the surfactant mixture of the present invention are combined in weight ratio a:b:c:d:e: of 2-4:0.5-1.5:0.5-1.5:0-.5-1.5:0-1.5. Most preferably, however, the components of the surfactant mixture of the present invention are combined in a weight ratio a:b:c:d:e of 2-4:1:1:1:1. Since each of the components of the surfactant mixture of the present invention is a dry powder, the resultant admixture is conveniently obtained in a dry powdered form.

Stable gas-in-liquid emulsions are obtained quite conveniently by forming at least a substantially saturated solution of the surfactant mixture in water or an oil-based medium and simply shaking the resultant admixture vigorously for from about 2 to about 10 seconds in air at room temperature (68° F.–77° F.) thereby forming high concentrations of stable gas microbubbles, i.e., a concentrated gas-in-liquid emulsion. Although the production of stable gas-in-liquid emulsions has been described herein in connection with air, simply forming at least a substantially saturated solution of the surfactant mixture of the present invention in water or in oil-based medium and shaking the resulting solution in the presence of any desired gaseous atmosphere from which a gas-in-liquid emulsion is desired will result in the formation of high concentrations of stable gas microbubbles by entrapping the particular gaseous medium of interest.

The following examples further illustrate the present invention. Unless otherwise stated, all percentages and parts are by weight.

EXAMPLE 1

A surfactant mixture was prepared in accordance with the present invention by admixing glycerol monolaurate, cholesterol benzoate, cholesterol, cholesterol acetate and glycerol tripalmitate in a weight ratio of 3:1:1:1:1, respectively, to obtain a dry powdery surfactant mixture.

EXAMPLE 2

A saturated solution of the surfactant mixture obtained in accordance with Example 1 was formed by admixing 0.1 gm of the surfactant mixture with 100 cc of water. (It is useful to realize that the total surfactant concentration is well above the critical micelle concentration, needed to form mixed micelles, but is preferably below the point of significant phase separation.) The resultant saturated solution was shaken vigorously for 4 seconds in air at 75° F. forming high concentrations of stable gas microbubbles. The microbubbles persisted for no less than 4.5 hours.

EXAMPLE 3

A dry surfactant mixture in accordance with the present invention was obtained by admixing glycerol monopalmitate, lanosterol benzoate, sodium cholate, cholesterol glucuronide, and stearoyl alcohol in a weight ratio of 4:1:1:1:1. A dry powdery surfactant mixture was obtained.

EXAMPLE 4

A saturated solution of the surfactant mixture obtained in Example 3 was formed by admixing 0.2 gm of the surfactant mixture with 100 cc of mineral oil. The resulting saturated solution was shaken vigorously for 5 seconds in air at 77° F. to form high concentrations of stable gas microbubbles. The microbubbles persisted for no less than 6 hours.

In the drawing, the sole figure graphically illustrates the particle size distribution obtained from dynamic-light-scattering measurements (i.e., photon correlation spectroscopy using a Coulter Model N4 Sub-Micron Particle Analyzer) of the saturated surfactant solution described in Example 2. The left peak (mean=196 nm or 0.196 μm) represents rod-like micelles of the surfactant mixture, whereas the larger-diameter uniform-sized particles comprising the narrower peak to the right (mean=1,150 nm) represent stable gas microbubbles. The stable microbubbles and micelles were observed to coexist in the saturated surfactant solution indefinitely, i.e., for at least several hours. Control measurements on distilled water alone resulted in no particles being detected at all within the diameter range of 30–10,000 nm.

That the population of larger-diameter particles (i.e., the right peak in the drawing), detected in these measurements on the surfactant solution described in Example 2, are indeed stable microbubbles is supported as follows: (1) The surfactant solution, prior to shaking, was passed through a precleaned membrane filter which removed all solid debris greater than 450 nm in diameter; (2) since none of the surfactants used are liquids, oil-in-water microemulsions or emulsions cannot be the basis for the existence of the larger-diameter population (or even the smaller-diameter population) of particles detected; (3) in accompanying decompression tests, it was found, in the course of developing the surfactant mixture described in Example 1, that those surfactant solutions which produced the higher concentrations of growing bubbles upon decompression (i.e., below 1 atm) similarly produced the greater degree of light scatter in the absence of decompression; and (4) the detection of the larger-diameter peak in the surfactant solution is extremely unlikely to be an artifact of the measurement technique since this second peak persisted indefinitely, the accompanying dust reading was 0%, and both peaks were not present in distilled water alone.

An estimate of the actual concentration of synthetic stable microbubbles, present in the preshaken surfactant solution described in Example 2, has been obtained from parallel experiments using a laser-based flow cytometer. This instrument presents particles (or microbubbles) in liquid suspension to a laminar flow cell in single file and, subsequently, counts individual particles using light scatter measurements sensitive to particle sizes down to 300 nm in diameter. Using the above-described surfactant solution, 360–400 particles/sec were consistently detected at a flow rate of approximately 1 cc/30 min. Therefore, the calculated concentration of synthetic microbubbles in the saturated surfactant solution described in Example 2 is approximately 700,000 microbubbles/cc. (It should be realized, however, that by varying the specific components and/or ratio of components of the surfactant mixture and/or the microbubble-forming conditions, e.g., forming a substantially saturated solution, a saturated solution, or a solution in excess of saturation, it becomes possible to change microbubble concentration severalfold and/or increase mean microbubble size up to about 10,000 nm (i.e., 10 μm).)

The stable gas microbubbles of substantially uniform diameter obtained in accordance with the present invention are particularly useful as contrast agents in echocardiography. Studies with air microbubbles formed by agitation of aqueous dextrose solutions have shown that echocardiographic contrast produced by microbubbles is useful in the qualitative analysis of intracardiac blood velocity and valvular regurgitation. In the past, microbubbles have been introduced into the blood stream via an intravenous catheter inserted into an antecubital vein. Echocardiographic recording is started and generally 100 cc of 5% aqueous dextrose solution is injected intravenously to produce right-sided contrast. While this procedure is usually sufficient to obtain adequate contrast, further contrast enhancement can be obtained by agitating the dextrose solution in the syringe with 1 to 2 cc of air and excluding all visible air prior to injection. In a small number of subjects in whom adequate contrast is still not obtained by this method, 1 to 2 cc of the subject's blood can be withdrawn and agitated with 6 cc of dextrose solution and 1 to 2 cc of air. Thereafter, all visible air is excluded and the resulting microbubbles are injected. (see, for example, Shiina A. et al., (1981), *Circulation* 63: 1408–1416;

Meltzer, R. S., et al., (1983), *Br. Heart J.* 49: 244–249; Levine, R. A., et al., (1984) *J. Am. Col. Cardiol.* 3:28-33). It is important to realize that there is a potential for variability in microbubble size based on subtle variations in injection technique and perhaps, the distance between the injection site and the heart. Potential introduction of larger microbubbles might provide a different spectrum of velocities. Because the size spectrum of microbubbles actually imaged in the heart is unknown, the significance of this potential source of variability is currently unclear. All of the above mentioned sources of variability could be greatly reduced or eliminated by the use of microbubbles which are stable i.e., long-lived, of controlled and uniform size, and non-toxic (see, for example, Feinstein, S., et al, (1984), *Clinical Research,* 32, No. 2: 163 A). In accordance with the present invention, a minimal amount of the surfactant mixture of the present invention is easily included in a syringe in which the microbubbles are to be produced by agitation with air and injected into the blood stream as described herein.

The emulsions of the present invention can also be produced in oil-based media. For example, using the same simple agitation procedure and the surfactant mixture of the present invention as described herein stable gas-in-liquid emulsions in oil based media such as mineral oil, hydrocarbon oil, petroleum distillates, vegetable oils, and the like are readily obtained. The stable gas microbubbles of the present invention in oil-based media is useful in explosive formulations for the mining industry. Hollow glass microspheres have heretofore been employed in slurries of a given explosive replacing much of the dangerous sensitizers employed therein. The result is an explosive which is cheaper and safer than dynamite. The stable gas microbubbles obtained in accordance with the present invention can replace these glass microspheres at considerable cost savings. Typically, ammonium nitrate is mixed with a variety of materials such as coals, oils, other carbonaceous materials and aluminum; organic nitrates and nitrocompounds, e.g. nitroglycerin, for sensitization; water, and a gelling agent to obtain a slurry which can be factory packed into typical explosive sticks or can be mixed in bulk at the site and pumped into place. The problem which has heretofore plagued the explosives industry is the extreme sensitivity of the sensitizers employed. Glass microspheres encompassing bubbles of air have been used or have been admixed in slurries and dispersions of the explosive replacing much of the sensitizers thereby eliminating significantly expensive and oftentimes, hazardous and toxic materials in the slurry. In use, when the blasting cap initiates the explosion, a basically adibatic compression occurs throughout the charge causing an exothermic reaction and compression of the glass microspheres. The dispersion of the glass microspheres throughout the slurry provides a mechanism by which the exothermic reaction spreads uniformly from one end of the charge to the other producing significant pressure and shattering action. The surfactant-stabilized gas microbubbles of the present invention can be employed to replace the significantly more expensive glass microspheres heretofore employed in lieu of the dangerous sensitizers in explosive mixtures.

What is claimed is:

1. A surfactant mixture for the production of stable gas-in-liquid emulsions comprising:
    (a) a member selected from the group consisting of glycerol monoesters of saturated carboxylic acids containing from about 10 to about 18 carbon atoms and aliphatic acohols containing from about 10 to about 18 carbon atoms;
    (b) a sterol-aromatic acid ester;
    (c) a member selected from the group consisting of sterols, terpenes, bile acids and alkali metal salts of bile acids;
    (d) a member selected from the group consisting of sterol esters of aliphatic acids containing from 1 to about 18 carbon atoms; sterol esters of sugar acids; esters of sugar acids and aliphatic alcohols containing from about 10 to about 18 carbon atoms; esters of sugars and aliphatic acids containing from about 10 to about 18 carbon atoms; sugar acids; saponins; and sapogenins; and
    (e) a member selected from the group consisting of glycerol, glycerol di- or triesters of aliphatic acids containing from about 10 to about 18 carbon atoms and aliphatic alcohols containing from about 10 to about 18 carbon atoms;
    said components being present in said mixture in a weight ratio a:b:c:d:e of 2–4:0.5–1.5:0.5–1.5:0–1.5:0–1.5.

2. A surfactant mixture for the production of stable gas-in-liquid emulsions as defined in claim 1 wherein the weight ratio a:b:c:d:e ranges from 2–4:0.5–1.5:0.5–1.5:0-.5–1.5:0–1.5.

3. A surfactant mixture as defined in claim 1 wherein the weight ratio a:b:c:d:e ranges from 2–4:1:1:1:1.

4. A surfactant mixture as defined in claim 1 consisting essentially of glycerol monolaurate, cholesterol benzoate, cholesterol, cholesterol acetate and glycerol tripalmitate in a weight ratio of 2–4:1:1:1:1.

5. A process for the preparation of stable gas microbubbles in aqueous or oil-based media comprising:
    forming at least a substantially saturated solution of a surfactant mixture comprising:
    (a) a member selected from the group consisting of glycerol monoesters of saturated carboxylic acids containing from about 10 to about 18 carbon atoms and aliphatic alcohols containing from about 10 to about 18 carbon atoms;
    (b) a sterol-aromatic acid ester;
    (c) a member selected from the group consisting of sterols, terpenes, bile acids and alkali metal salts of bile acids;
    (d) a member selected from the group consisting of sterol esters of aliphatic acids containing from 1 to about 18 carbon atoms; sterol esters of sugar acids; esters of sugar acids and aliphatic alcohols containing from about 10 to about 18 carbon atoms; esters of sugars and aliphatic acids containing from about 10 to about 18 carbon atoms; sugar acids; saponins; and sapogenins; and
    (e) A member selected from the group consisting of glycerol, glycerol di- or triesters of aliphatic acids containing from about 10 to about 18 carbon atoms and aliphatic alcohols containing from about 10 to about 18 carbon atoms;
    said components being present in said mixture in a weight ratio a:b:c:d:e of 2–4:0.5–1.5:0.5–1.5:0–1.5:0–1.5; in an aqueous or oil-based medium;
    shaking said substantially saturated solution of the surfactant mixture for from about 2 to about 10 seconds in the gaseous atmosphere at room temperature, thereby forming a concentrated gas-in-liquid emulsion.

6. Process as defined in claim 5 wherein the substantially saturated solution is formed in an aqueous medium.

7. Process as defined in claim 5 wherein the substantially saturated solution is formed in an oil-based medium.

8. Process as defined in claim 5 wherein the substantially saturated solution is formed by admixing from about 0.02 to about 0.4 gm of said surfactant mixture with 100 cc. of an aqueous or oil-based medium.

9. A process as defined in claim 5 wherein said components are present in said surfactant mixture in the weight ratio a:b:c:d:e of 2–4:0.5–1.5:0.5–1.5:0.5–1.5:0–1.5.

10. A process as defined in claim 5 wherein said components are present in said surfactant mixture in the weight ratio a:b:c:d:e of 2–4:1:1:1:1.

11. A stable gas-in-liquid emulsion obtained by the process of claim 5.

12. A stable gas-in-liquid emulsion obtained by the process of claim 6.

13. A stable gas-in-liquid emulsion obtained by the process of claim 7.

* * * * *

UNITED STATES PATENT AND TRADEMARK OFFICE
CERTIFICATE OF CORRECTION

PATENT NO. : 4,684,479
DATED : August 4, 1987
INVENTOR(S) : Joseph S. D'Arrigo

It is certified that error appears in the above-identified patent and that said Letters Patent is hereby corrected as shown below:

Column 8, claim 1, line 2, "acohols" should read -- alcohols --.

Signed and Sealed this

Eighth Day of December, 1987

Attest:

DONALD J. QUIGG

Attesting Officer

Commissioner of Patents and Trademarks